United States Patent
Lee et al.

(10) Patent No.: US 8,094,013 B1
(45) Date of Patent: Jan. 10, 2012

(54) BABY MONITORING SYSTEM

(76) Inventors: Taek Kyu Lee, La Mirada, CA (US);
Min Soo Han, Irvine, CA (US)

( * ) Notice: Subject to any disclaimer, the term of this patent is extended or adjusted under 35 U.S.C. 154(b) by 373 days.

(21) Appl. No.: 12/415,035

(22) Filed: Mar. 31, 2009

(51) Int. Cl.
*G08B 1/08* (2006.01)
(52) U.S. Cl. .................... 340/539.15; 340/586
(58) Field of Classification Search ............ 340/539.15, 340/573, 586; 600/25
See application file for complete search history.

(56) References Cited

U.S. PATENT DOCUMENTS

| | | | |
|---|---|---|---|
| 4,146,885 A | 3/1979 | Lawson, Jr. | |
| 5,022,402 A | 6/1991 | Schieberl et al. | |
| 5,515,865 A | 5/1996 | Scanlon | |
| 5,684,460 A | 11/1997 | Scanlon | |
| 5,853,005 A * | 12/1998 | Scanlon | 600/459 |
| 6,011,477 A | 1/2000 | Teodorescu et al. | |
| 6,150,941 A | 11/2000 | Geiger et al. | |
| 6,485,441 B2 | 11/2002 | Woodward | |
| 6,847,892 B2 | 1/2005 | Zhou et al. | |
| 7,420,472 B2 | 9/2008 | Tran | |
| 2005/0277842 A1 | 12/2005 | Silva | |
| 2007/0296571 A1 | 12/2007 | Kolen | |
| 2008/0004904 A1 * | 1/2008 | Tran | 705/2 |
| 2008/0015457 A1 | 1/2008 | Silva | |
| 2008/0252445 A1 | 10/2008 | Kolen | |
| 2008/0262381 A1 | 10/2008 | Kolen | |
| 2008/0294019 A1 | 11/2008 | Tran | |
| 2008/0319282 A1 | 12/2008 | Tran | |

* cited by examiner

*Primary Examiner* — Shirley Lu
(74) *Attorney, Agent, or Firm* — Mind Law Firm; Justin G. Sanders; Jeromye V. Sartain

(57) ABSTRACT

A baby monitoring system for remotely monitoring a child's breath rate and body orientation is disclosed. The system comprises, in one embodiment, a parent unit retained by a supervisor, a sensor unit removably engaged around the child's abdomen, and a nursery unit positioned proximal the child, preferably in the same room. The sensor unit provides at least two tri-axial accelerometers positioned and configured such that each is independently capable of measuring both the child's breath rate and body orientation, even where the child's body is oriented such that movement of at least one of the accelerometers is restricted. The sensor unit then wirelessly transmits this information to the nursery unit, which performs necessary calculations and transmits this data to the parent unit, which displays the data on a display screen. Additionally, the system is capable of recording and reproducing a heart beat sound of the child's mother.

12 Claims, 4 Drawing Sheets

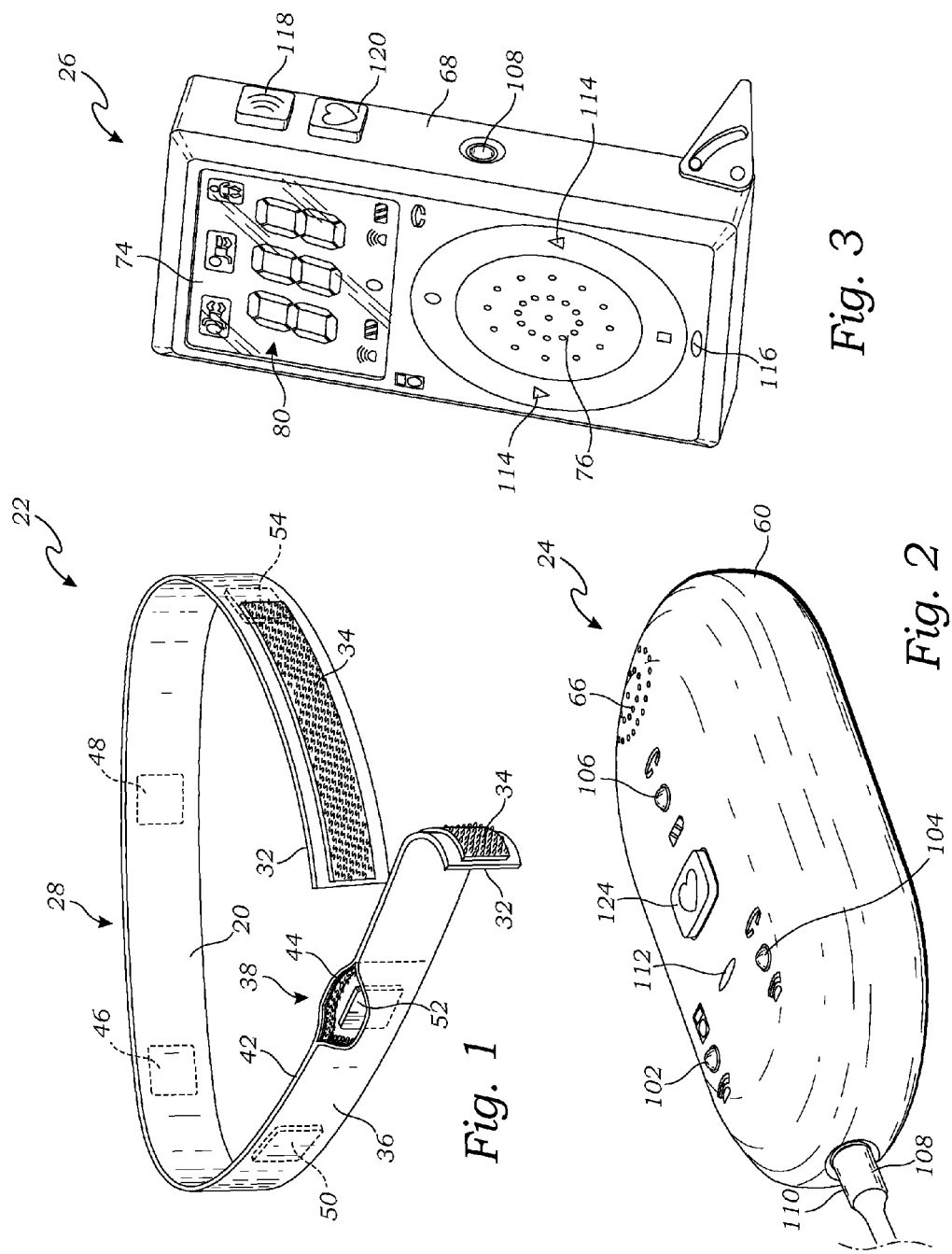

BABY MONITORING SYSTEM

RELATED APPLICATIONS

Not applicable.

INCORPORATION BY REFERENCE

Applicant(s) hereby incorporate herein by reference any and all U.S. patents and U.S. patent applications cited or referred to in this application.

BACKGROUND OF THE INVENTION

1. Field of the Invention

Aspects of this invention relate generally to baby monitors, and more particularly to a baby monitoring system for measuring the breath rate and body orientation of a child or infant using accelerometer technology.

2. Description of Related Art

Baby monitors are well known. Such monitors typically comprise either video cameras and/or audio microphones that are placed in close proximity to the child which transmit a signal to a remote video monitor and/or speaker to thus provide the supervising caregiver with a visual and/or audio signal to the alert the caregiver that the child is uncomfortable or in distress. With respect to most prior art auditory systems that Applicants are aware of, such systems are designed to merely reproduce the sounds emanating from the child, such as crying, coughing and/or choking, which serve as the basis to warn the supervising caregiver that attention is needed.

Although generally effective in monitoring the condition of a child from a remote location, most prior art systems currently in use suffer from numerous drawbacks. With respect to video monitoring systems, it is known that the cameras utilized are typically mounted in a fixed position and can only monitor a limited area. As such, to the extent the child strays from that field of vision, or is covered in bedding, these video monitoring systems are ineffective. Similarly, acoustic monitoring systems suffer from the drawbacks of not providing consistent, uniform and dependable monitoring of a child. In this regard, such systems are based upon the child producing an audible signal when in distress or discomfort. However, such systems fail to address a number of situations where a supervising caregiver must necessarily be warned about conditions beyond those sounds generated in the child's environment. For example, such audio monitors fail to provide any indication should the child quietly leave their bed or simply stop breathing, which occurs with Sudden Infant Death Syndrome (SIDS) where a healthy infant dies suddenly during sleep, for no apparent reason. Accordingly, there is a strong need for a child monitoring system which can detect the physiological presence of a living child/infant.

The following art defines the present state of this field:

U.S. Pat. No. 4,146,885 to Lawson, Jr. discloses a hospital bed or mattress for neonatal infants with a respiration monitor and alarm to detect apnea. No sensor or other appliance is attached to the infant. The bed comprises a base or frame structure with a soft resilient membranous top or cover, e.g., of sheet rubber. The closed air space below the pan is vented to the outside as by a small hole or tube, the average air pressure inside being about atmospheric. The baby's breathing causes slight rhythmic displacements of portions of the body, which in turn transmit small dynamic "recoil" forces proportional to acceleration to the flexible membrane on which the baby rests. The resulting diaphragm-like displacements modulate the air pressure inside. Breathing is sensed by monitoring this acoustic signal by a vented pressure microphone or by sensitive anemometer means connected to the vent. Acoustic and electrical filtering are used to discriminate against higher-frequency signals from the heart-beat and from ambient vibration. Cessation of the respiration signal for a predetermined period of time actuates an alarm.

U.S. Pat. No. 5,022,402 to Schieberl et al. discloses a medical monitoring device which monitors the pulse and respiration rate of an infant, and transmits an alarm signal to a remote receiver when pulse and/or respiration rate irregularities are detected. The device incorporates an acoustic sensor (microphone) and pressure sensor adjacent a small gas or liquid-filled bag or bladder member. The bladder member and attached sensors are contained in a compact monitor housing which is positioned against the monitored infant's body, so that the bladder member directly contacts the body, and is preferably held in place by a small belt wrapped around the infant.

U.S. Pat. No. 5,515,865 to Scanlon discloses a movement and sound monitor and stimulator which is particularly useful for preventing death in human infants from sudden infant death syndrome. The movement and sound monitor and stimulator has a base member which may be a fluid-filled sensing pad for supporting the infant or other animate object which is being monitored and a transducer positioned for detecting movement or acoustic activity (e.g., heartbeat, breathing) of the object on the base member to provide an output signal in response to forces applied thereto which are generated by such movement. A circuit is connected to monitor the output signal from the transducer and activates a stimulator which is operable to provide movement to the base member to stimulate movement in the object when output from the transducer to the circuit corresponds to no movement from the object. The transducer may be a pressure transducer in fluid communication with the fluid interior of the sensing pad. In the alternative, a piezo-electric sheet operatively connected to a surface of the sensing pad to detect such movement as well as movement cessation. The circuit may also be connected to an alarm which can provide an audible or visual indication to third parties when there is no movement from the object.

U.S. Pat. No. 5,684,460 to Scanlon discloses a movement monitor and stimulator which may prevent death in human infants from sudden infant death syndrome (SIDS). Recent medical studies indicate a SIDS victim's breathing may be resuscitated by immediate stimulation. The sound and/or movement monitor and stimulator may have a base member configured as a fluid-filled sensing pad for supporting an infant and a transducer for detecting movement or acoustic activity (e.g., heart beat, breathing, voice and motion sounds). A stimulator may move the base member to stimulate movement in the object when output from the transducer corresponds to no sound and/or movement from the object, or indicates a dangerous change in monitored condition, such as the decrease in metabolic rate indicative of the onset of sleep. The stimulator may also be applied in a more gentle fashion to soothe and quiet an infant that has been awakened unexpectedly. The transducer may be a pressure transducer in fluid communication with the fluid interior of the sensing pad. Alternatively, a piezoelectric sheet operatively connected to a surface of the sensing pad may detect movement and movement cessation. An alarm may provide an audible and/or visual indication to third parties when there is no movement from the object. A transmitter may continuously transmit the sensor's output to a remote location for monitoring. A remote monitor may transmit heart and breathing sounds and may also have lights indicating motion and acoustic activity to indicate the infant is breathing.

U.S. Pat. No. 6,011,477 to Teodorescu et al. discloses a monitoring system which includes a first sensor for detecting the respiration and/or movements of an infant, and an optional second sensor for detecting the presence and/or movement of the infant or proximal objects surrounding the infant. An optional accelerometric sensor detects movements of a platform supporting the infant and contributes supplementary movement data to the monitoring system. An optional audio sensor detects sounds associated with the infant or proximal objects. None of the sensors are physically attached to the infant. A controller conditions and processes the various sensor signals and generates alarms by interpreting the sensor signals. The controller optionally communicates with a remote control unit. In one embodiment the first sensor signal is filtered to extract respiration- and nonrespiration-related signals that are processed by a signal processor, which compares the extracted signals to thresholds, and if neither signal exceeds its threshold for a predetermined time, a low signal alarm is generated. In another embodiment, the signal processor determines whether a respiration decay period is less than a threshold value, and if not, generates a respiration decay alarm. In yet another embodiment, the signal processor compares the respiration-related signal pattern to a stored pattern, and if the patterns do not match, a respiration pattern alarm is generated. The signal processor further interprets various combinations of the sensor signals and makes aggregated decisions to generate specific warnings when critical situations occur.

U.S. Pat. No. 6,150,941 to Geiger et al. discloses a stand-off, non-invasive acoustic detector for monitoring physical activity and/or breathing activity of children and infants. According to a preferred embodiment, the present invention comprises a two-phase output oscillator coupled to an ultrasonic transmitter and microphone. A respective one of the outputs of the oscillator drives the ultrasonic transmitter, through a power amplifier, which sends out an ultrasound wave. The echo return is picked up by the microphone and thereafter band passed to isolate those frequencies falling within 33 to 40 kHz. Such signal is further adjusted for automatic gain control. The resultant echo return signal is compared to the respective other output of the oscillator, the latter also being adjusted for automatic gain control, which are then combined via a summing junction to produce a resultant signal, the latter being utilized to drive a phase comparator and an alarm timer. To the extent the resultant signal, which corresponds to continuous breathing activity or physical activity, deviates substantially from the signal produced by the comparator for a sufficient length of time, an alarm is activated to signal either abnormal breathing activity or a lack of breathing activity, the latter indicative of either a medical condition, such as SIDS, or the absence of the child from the monitored area.

U.S. Pat. No. 6,485,441 to Woodward discloses a mattress device which provides a high information variety from a low number of sensors configured and placed in correspondence with a mattress core layer and a mattress top layer of the mattress device in order to monitor a patient's sleep behavior. Mattress core and top layers provide a static position transmission characteristic and a dynamic impulse transmission characteristic enabling the sensors to recognize body imprint position and body impulses induced by the sleeping patient with a broad bandwidth. In an alternate embodiment, the mattress device may be combined with a signal coder capable of receiving signals or signal components from the sensors and transform them in an analog signal that can be received and processed by a conventional sound card of a computer. A decoding program installed on the computer decodes the alphanumeric information processed from the analog signal by the sound card and makes it available for further interpretation.

U.S. Pat. No. 6,847,892 to Zhou et al. discloses a remote device that includes a sensor for determining or measuring a desired parameter, a receiver for receiving position data from the Global Positioning System (GPS) satellite system, a processor for determining whether or not alert conditions are present and a wireless transceiver for transmitting the measured parameter data and the position data to a central station, such as an application service provider (ASP). The ASP, in turn, may communicate the measured data, position data and notification of any alerts to an end user via an alert device. The present invention also relates to various applications and systems utilizing the capabilities of such a device.

U.S. Patent Application Publication No. 2005/0277842 to Silva discloses a monitor respiration movements device to be used on humans and also on animals for controlling the respiration movements and specially to control the apnea periods on infants. Furthermore the present invention is related to reduce the mortality rate caused by the sudden instant death syndrome (SIDS). The device comprises an accelerometer and a micro controller, said accelerometer includes a motion detector and a plurality of output plugs, said micro controller includes a plurality of input sockets, wherein said plurality of output plugs are connected so said plurality of input sockets and the micro controller includes signal outputs which are connected to an alarm means.

U.S. Patent Application Publication No. 2007/0296571 to Kolen discloses techniques and systems that monitor motion of a person or object and wirelessly communicate the motion data of the person through a network of wireless communication transceiver nodes to a central monitor station. An abnormal state of motion of the person or object can be detected based on the motion data and an alert signal can be generated when an abnormal condition of the person or object occurs. Other parameters of a person or object may also be measured and transmitted to the central monitor station, such as the heart beat and body temperature of the person or the orientation or dynamic motion of an object.

U.S. Patent Application Publication No. 2008/0015457 to Silva discloses a monitor respiration movements device to be used on humans and also on animals for controlling the respiration movements and to control the apnea periods on infants, wherein the device reduces the mortality rate caused by the sudden instant death syndrome (SIDS), wherein the device comprises an accelerometer and a micro controller, with the accelerometer including a motion detector and a plurality of output plugs, the micro controller includes a plurality of input sockets, and wherein the plurality of output plugs are connected to the plurality of input sockets and the micro controller includes signal outputs which are connected to an alarm.

U.S. Pat. No. 7,420,472 to Tran discloses a monitoring system which includes one or more cameras to determine a three dimensional (3D) model of a person, means to detect a dangerous condition based on the 3D model, and means to generate a warning when the dangerous condition is detected.

U.S. Patent Application Publication No. 2008/0252445 to Kolen discloses techniques, apparatus and wireless sensing networks for using wireless sensor modules positioned at different locations to obtain data of a person, an object or a premise and to form a dynamically configurable wireless sensing network where each wireless sensor module is wirelessly connected to the network and can be automatically added to or removed from the wireless sensing network.

U.S. Patent Application Publication No. 2008/0262381 to Kolen discloses techniques, devices and systems that monitor the orientation and breathing of an infant and wirelessly communicate the orientation/breathing data to a caregiver through a wireless interface to request intervention if an unsafe situation is detected.

U.S. Patent Application Publication No. 2008/0294019 to Tran discloses a monitoring system which includes wireless local area network (WLAN) transceivers operating as a Doppler radar to wirelessly detect the person's heart parameter, and a processor coupled to the WLAN transceivers to determine a stroke attack.

U.S. Patent Application Publication No. 2008/0319282 to Tran discloses a monitoring system for a person in a building which includes a plurality of wireless bases positioned in the building, a body mounted temperature sensor, a body mounted heart signal sensor, a wearable device coupled to the temperature sensor and to the heart signal sensor and having a wireless transceiver adapted to communicate with the wireless bases, and an accelerometer.

The prior art described above teaches baby monitoring devices and systems configured for measuring the breath rate and/or body orientation of a child using various technologies, including accelerometer technology. However, the prior art fails to teach such a system that provides at least two tri-axial accelerometers positioned on the child's body and configured such that each accelerometer is independently capable of measuring both the child's breath rate and body orientation, even where the child's body is oriented such that movement of at least one of the accelerometers is restricted. Additionally, the prior art fails to teach such a system capable of recording and reproducing a heart beat sound of the child's mother. Aspects of the present invention fulfill these needs and provide further related advantages as described in the following summary.

SUMMARY OF THE INVENTION

Aspects of the present invention teach certain benefits in construction and use which give rise to the exemplary advantages described below.

The present invention solves the problems described above by providing a baby monitoring system which comprises, in one embodiment, a sensor unit, a nursery unit and a parent unit. The parent unit is retained by the supervisory caregiver. Preferably, the sensor unit is contained in a removably engagable strap that can be easily engaged around the child's abdomen over their clothing to continuously monitor breath rate and body orientation. The nursery unit is positioned proximal the child, preferably in the same room. The sensor unit uses at least two tri-axial accelerometers to measure accelerations of the child's abdomen movement and their body orientation. The sensor unit then wirelessly transmits this information to the nursery unit, preferably via RF signals. The nursery unit then uses this information to calculate the child's breath rate and body orientation and transmits this data to the parent unit, which displays the data on a display screen. Thus, the present invention allows a supervisory caregiver to remotely monitor the child's breath rate and body orientation from another room, or from an even greater distance.

In another aspect, the system is capable of generating an artificial heart beat sound through a speaker located in the nursery unit. In yet another aspect, the parent unit provides a speaker interconnected with a microphone located in at least one of the sensor unit or nursery unit, enabling the supervisory caregiver to hear any audible noises coming from the child's room in addition to the other data being received regarding the child's breath rate and position as described above.

A primary objective inherent in the above described system is to provide advantages not taught by the prior art.

Another objective is to provide such a system that is capable of measuring the breath rate and body orientation of a child using accelerometer technology.

A further objective is to provide such a system that is capable of functioning properly regardless of the child's body orientation.

A still further objective is to provide such a system that is configured to not disturb the child while the child rests.

A still further objective is to provide such a system that generates appropriate, user-friendly visual and/or audible alerts to a supervisor when an alert situation is detected.

A still further objective is to provide such a system that displays status information for allowing the supervisor to quickly and easily determine whether each component of the system is functioning properly.

A still further objective is to provide such a system that is capable of recording and reproducing a heart beat sound of the child's mother.

Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The accompanying drawings illustrate aspects of the present invention. In such drawings:

FIG. 1 is a perspective view of a sensor unit of an exemplary embodiment of the present invention;

FIG. 2 is an enlarged perspective view of a nursery unit of an exemplary embodiment of the invention;

FIG. 3 is an enlarged perspective view of a parent unit of an exemplary embodiment of the invention;

DETAILED DESCRIPTION OF THE INVENTION

The above described drawing figures illustrate aspects of the invention in at least one of its exemplary embodiments, which are further defined in detail in the following description.

Described now in detail is a baby monitoring system for measuring the breath rate and body orientation of a child or infant, hereafter referred to simply as a child 20, using accelerometer technology. As shown in FIGS. 1-3, aspects of the system comprise, in the exemplary embodiment, a sensor unit 22 (FIG. 1), a nursery unit 24 (FIG. 2), and a parent unit 26 (FIG. 3). Preferably, each of the sensor unit 22, nursery unit 24, and parent unit 26 are in wireless communication with one another. In the exemplary embodiment, the wireless communication operates on the ZigBee® protocol, which was designed to address the market need for a cost-effective, standards-based wireless networking solution that supports low data rates, low power consumption, security, and reliability. It should be noted that other wireless or wired communication protocols, now known or later developed, may be substituted.

Figure 4:
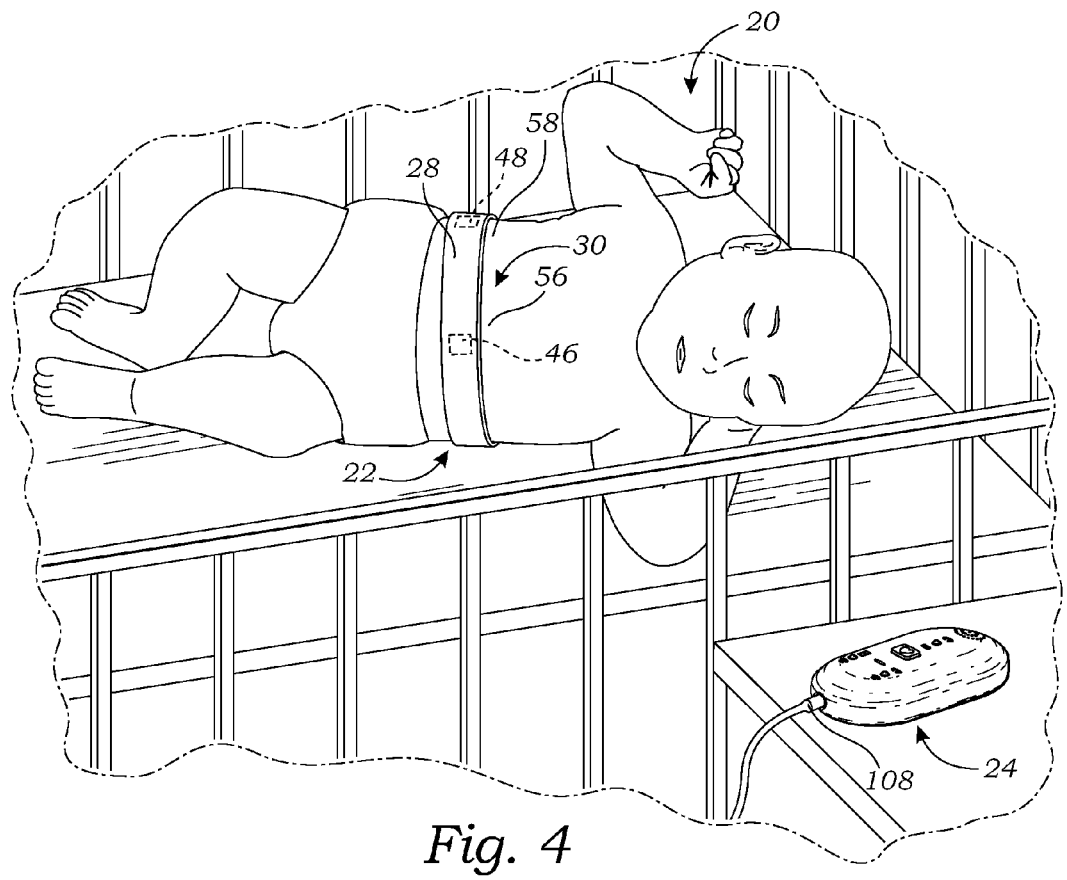
FIG. 4 is a perspective view of a child wearing the exemplary sensor unit, with the exemplary nursery unit proximal the child's location.

As shown in FIG. 1, the sensor unit 22 comprises an elongate strap 28 configured for removable engagement around the child's abdomen 30. Preferably, the strap 28 is made of a soft, lightweight, flexible material, such as cotton or microfiber; however, other types of materials, now known or later developed, may be substituted. Each of the strap 28's opposing ends 32 provides a means for removable engagement 34, such that the strap 28 is able to be wrapped around the child's abdomen 30 and the ends 32 secured to one another, as illustrated in FIG. 4. The means for removable engagement 34 are preferably hook and loop fasteners; however, other types of temporary engagement means, now known or later developed, such as buttons, may be substituted.

In the exemplary embodiment, as best shown in FIG. 1, the strap 28 comprises a pair of opposing strap pieces 36 which are secured together, forming a pocket 38 therebetween. In one embodiment, an edge 42 of the strap 28 provides a means 44 for selectively opening the pocket 38, such as hook and loop fasteners. It should be noted that other means for selectively opening the pocket 38, now known or later developed, may be substituted. In an alternate embodiment, the strap pieces 36 are completely secured together, thereby preventing access to the pocket 38 after the present invention is manufactured.

Referring still to FIG. 1, the strap 28 provides at least two tri-axial accelerometers 46 and 48, a sensor processor 50, a sensor transceiver 52, and a sensor power supply 54, each of which is positioned within the pocket 38. The accelerometers 46 and 48 are positioned such that, when the strap 28 is engaged around the child's abdomen 30, a first accelerometer 46 is in a location proximal the child's belly button 56, and a second accelerometer 48 is in a location proximal the child's side 58, as shown in FIG. 4. The monitoring of breath rate is accomplished by measuring the movements of the child's abdomen 30. As the child 20 inhales and exhales, the abdomen 30 mechanically expands and contracts, respectively, which can be detected by the highly sensitive accelerometers 46 and 48. Because each one of the accelerometers 46 and 48 is a tri-axial accelerometer (i.e., capable of measuring accelerations in each of the orthogonal X, Y, and Z directions), each of the accelerometers 46 and 48 is independently capable of measuring the child's 20 breath rate. Thus, even if the child 20 is lying on its stomach or substantially face-down, for example, thereby restricting movement of the first accelerometer 46, the second accelerometer 48 would remain unrestricted and, therefore, capable of continuing to monitor the child's 20 breath rate. When both accelerometers 46 and 48 are unrestricted, the present invention is able to use both sets of data to more precisely determine the child's 20 breath rate and body orientation.

Additionally, because the accelerometers 46 and 48 are capable of measuring accelerations in each of the orthogonal X, Y, and Z directions, the child 20's body orientation is also able to be monitored. As such, the present invention is capable of detecting whether the child 20 is lying face down, lying face up, or even sitting up. It should be noted that, in further embodiments, more than two accelerometers may be used in the present invention.

Figure 5:
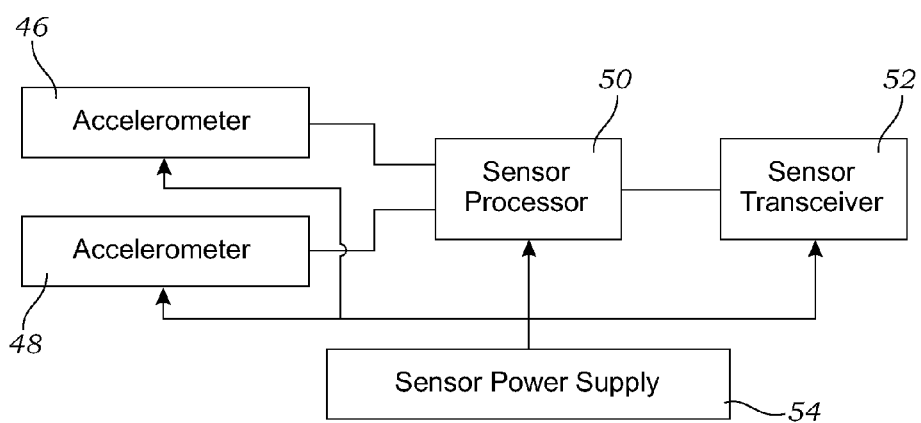
FIG. 5 is a schematic view of the exemplary sensor unit.

As shown in the schematic view of FIG. 5, the sensor processor 50 is interconnected with the accelerometers 46 and 48. As each of the accelerometers 46 and 48 collects data on the child's 20 breathing and body orientation, the data is output to the sensor processor 50. The sensor processor 50 is configured for receiving this output and packaging it into a sensor signal. The sensor transceiver 52, which is interconnected with the sensor processor 50, then transmits the sensor signal to the nursery unit 24. The sensor power supply 54 provides power to both accelerometers 46 and 48, the sensor processor 50, and the sensor transceiver 54. All such components of the sensor unit 22 may be wired or electrically interconnected in any suitable manner now known or later developed.

Figure 6:
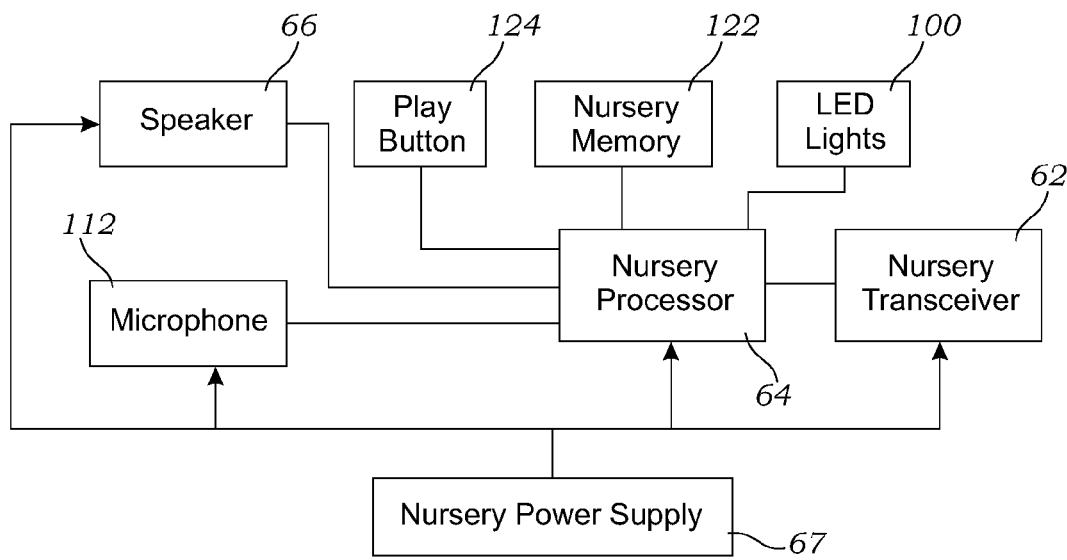
FIG. 6 is a schematic view of the exemplary nursery unit.

As shown in FIGS. 2 and 6, the nursery unit 24 comprises, in the exemplary embodiment, a relatively compact nursery unit housing 60, within which is contained a nursery transceiver 62, a nursery processor 64, a nursery speaker 66, and a nursery power supply 67. In order to accommodate the relatively short wireless range, and thus the low power consumption, of the ZigBee® protocol, the nursery unit 24 is preferably positioned in the same room as the sensor unit 22, proximal the child 20's location, as illustrated in FIG. 4. As shown in the schematic view of FIG. 6, the nursery transceiver 62 is interconnected with the nursery processor 64. Thus, as the nursery transceiver 62 receives the sensor signal from the sensor transceiver 52 (FIG. 5), it sends the sensor signal to the nursery processor 64. The nursery processor 64 is configured for processing the sensor signal in order to determine both the child 20's breath rate and body orientation. After determining the child 20's breath rate and body orientation, the nursery processor 64 then packages this data into a display signal, which the nursery transceiver 62 transmits to the remote parent unit 26. Again, the components of the nursery unit 24 may be wired or electrically interconnected in any suitable manner now known or later developed.

Figure 7:
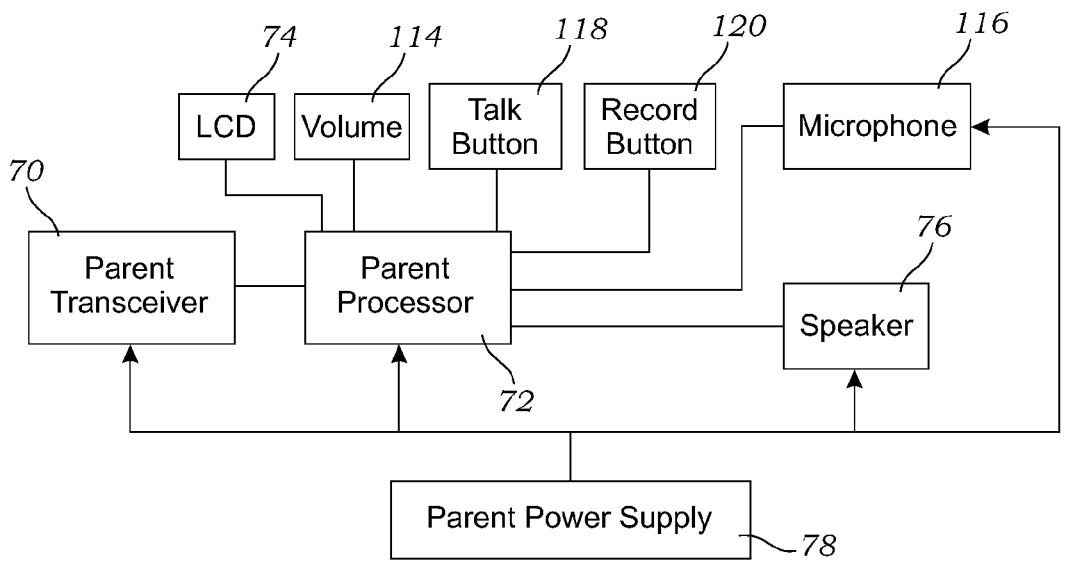
FIG. 7 is a schematic view of the exemplary parent unit.
Figure 8:
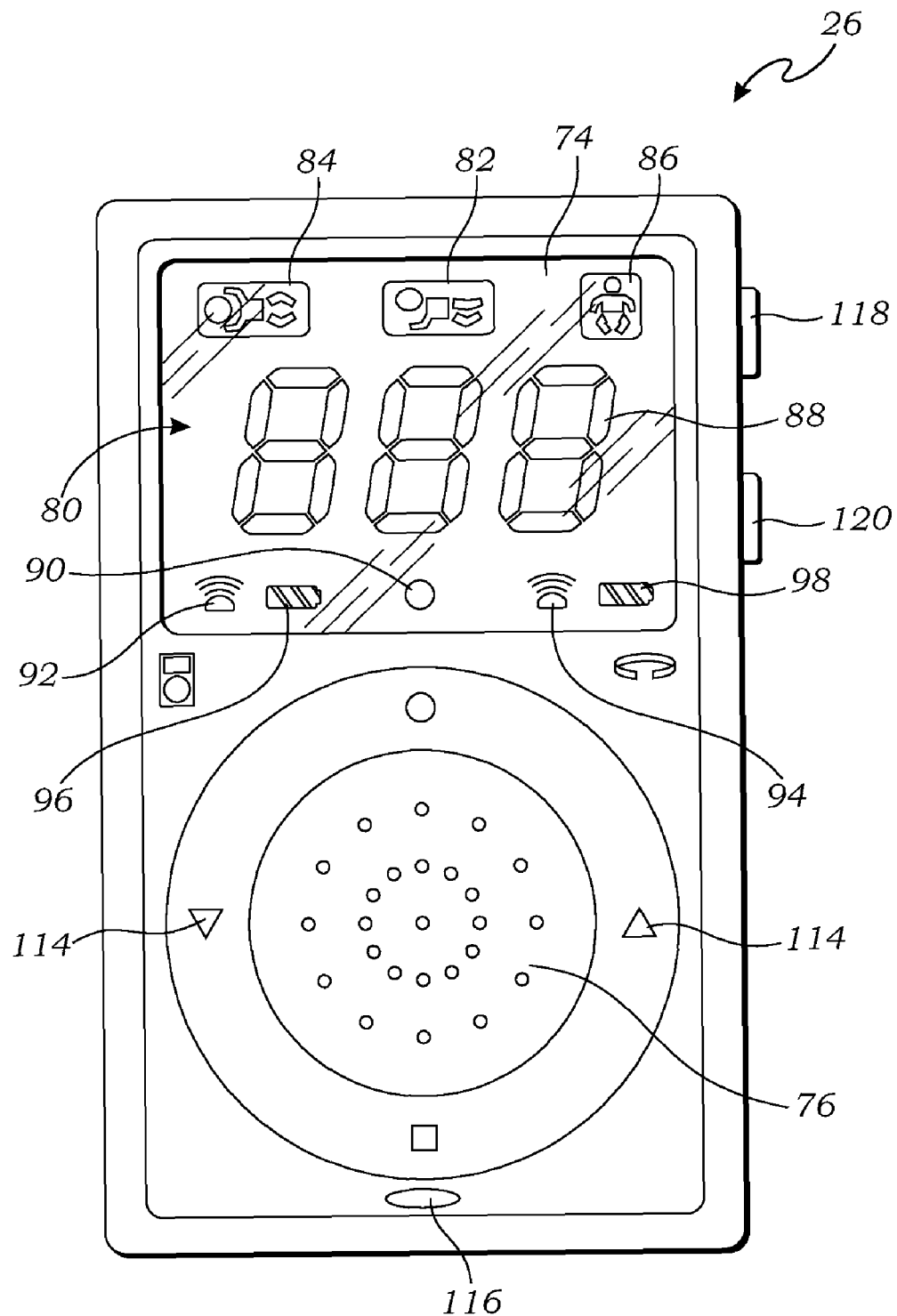
FIG. 8 is a plan view of the exemplary parent unit.

As shown in FIGS. 3 and 7, the parent unit 26 comprises, in the exemplary embodiment, a relatively compact and portable parent unit housing 68, within which is contained a parent transceiver 70, a parent processor 72, a display 74, a parent speaker 76, and a parent power supply 78. The parent unit 26 is maintained in the possession of a supervisory caregiver, hereafter referred to simply as a supervisor (not shown). As shown in the schematic view of FIG. 7, the parent transceiver 70 is interconnected with the parent processor 72. Thus, as the parent transceiver 70 receives the display signal from the nursery transceiver 62, it sends the display signal to the parent processor 72. The parent processor 72 is configured for processing the display signal and generating the appropriate display data 80. The display data 80 is then displayed on the display 74. The display 74 is preferably an LCD screen; however, other types of display screens or electronic devices that represent information in visual form, now known or later developed, may be substituted. An exemplary embodiment of the display 74 is best shown in FIG. 8. The display 74 provides a user-friendly interface, which reduces potential confusion and allows the supervisor to quickly and easily determine the child 20's current breath rate and body orientation at any given time. Once more, the components of the parent unit 26 may be wired or electrically interconnected in any suitable manner now known or later developed.

As shown in FIG. 8, if the child 20 is lying face down, a face-down icon 82 is displayed on the display 74; if the child 20 is lying face up, a face-up icon 84 is displayed; and if the child 20 is sitting up, a sitting-up icon 86 is displayed. With respect to the child 20's breath rate, a breath rate number 88 is displayed on the display 74 as well. Preferably, the breath rate number 88 is based on the number of breaths per minute. The parent unit 26 also preferably provides a breath rate light 90 configured for flashing in conjunction with the child's 20 breath rate, allowing the supervisor to see, in real time, just how fast or slow the child 20 is breathing. In one embodiment, the breath rate light 90 is an LED light integral with the parent unit housing 68. In another embodiment, the breath rate light 90 is displayed on the display 74, as shown in FIG. 8. It should be noted that the above described display arrangement is merely an exemplary embodiment to illustrate the present invention's underlying functionality. As such, the present invention itself is not intended to be so limited to the particular display arrangement described above.

In addition to displaying information related to the child 20's breath rate and body orientation, the display 74 also preferably displays other system status information. In the exemplary embodiment, shown best in FIG. 8, the display provides a parent unit signal meter 92, a sensor unit signal meter 94, a parent battery meter 96, and a sensor battery meter 98. In further embodiments, the display 74 may display additional information, such as the nursery unit 24's power status, and the sensor unit 22's power status. Thus, the supervisor is able to quickly and easily determine, by simply looking at the display 74, whether, and how well, each component of the system is functioning.

The onset of sudden infant death syndrome (SIDS) is suggested by research to be associated with a face-down sleeping position. However, a face-up sleeping position could be potentially dangerous as well, should the child 20 choke on fluids it brings up. If the nursery processor 64 detects such an alert situation (i.e., if the nursery processor 64 determines that the child 20 is lying face down, or the child's 20 breath rate slows to a dangerous rate), the nursery processor 64 generates an alert signal. The nursery speaker 66 is interconnected with the nursery processor 64 and configured for generating an audible alert whenever an alert signal is generated. An alert signal is also transmitted to the parent unit 26 upon which the parent speaker 76 will generate a similar audible alert to notify the supervisor of the potential emergency situation. Additionally, the display 74 may also display an appropriate alert message (not shown), such that the supervisor will be able to quickly and easily determine exactly why the alert was generated.

In the exemplary embodiment, as best shown in FIG. 2, the nursery unit housing 60 provides a plurality of indicator lights 100 for displaying various system status information. In the exemplary embodiment, shown best in FIG. 2, the nursery unit housing 60 provides a parent signal light 102, a sensor signal light 104, and a sensor battery light 106. In further embodiments, the nursery unit housing 60 may provide additional indicator lights 100 to display additional information, such as the parent unit 26's battery life, the parent unit 26's power status, and the sensor unit 22's power status. Preferably, each one of the indicator lights 100 is a multi-color LED light, capable of displaying different colors depending on the system status information. For example, with respect to the parent unit signal light 102, a red color indicates no wireless reception between the parent unit 26 and nursery unit 24, an orange color indicates weak wireless reception, and a green color indicates strong wireless reception. In alternate embodiments, other means for displaying system status information, now known or later developed, such as an LCD screen, may be substituted.

As briefly mentioned above, the sensor unit 22 and parent unit 26 are preferably battery-powered. As shown in FIGS. 1 and 5, the sensor power supply 54 is a flexible thin film rechargeable battery. Flexible thin film batteries are ideally suited for the sensor unit 22 due to the fact that the strap 28 will be removably engaged around the child's abdomen 30 while the child 20 sleeps, as illustrated in FIG. 4. Because flexible thin film batteries are capable of bending and conforming, the child 20 is able to sleep comfortably and is less likely to be bothered by the strap 28 or sensor power supply 54. In addition, thin film batteries have solid lithium cores rather than liquid cores, so they are less vulnerable to overheating and catching fire. They also lose virtually no power over time, and can be recharged thousands of times before they need to be replaced. While flexible thin film batteries have been shown and described, it will be appreciated by those skilled in the art that other batteries and battery technologies now known or later developed may be substituted without departing from the spirit and scope of the invention.

As shown in FIG. 7, the parent power supply 78 is preferably a small Lithium-Polymer rechargeable battery, while as shown schematically in FIG. 6, the nursery power supply 67 may be one or a combination of AC and DC power supplies. Specifically, as best shown in FIGS. 2-4, each of the nursery power supply 67 and parent power supply 78 preferably provide an AC jack 108 configured for receiving a AC adapter 110, thereby enabling each of the nursery unit 24 and parent unit 26 to operate on AC power as well as recharge the nursery power supply 67 and parent power supply 78, respectively, as needed. It should be noted, however, that other types of power supplies, now known or later developed, such as other types of rechargeable batteries or AC power, may be substituted. Additionally, similar recharging or AC power capability, in terms of the batteries themselves and/or the necessary jacks, adapters and the like, whether operable during use (while the child 20 is actually wearing the sensor unit 22) or when the sensor unit 22 is not being used, are all possible as part of the sensor unit 22, and the sensor power supply 54, specifically, without departing from the spirit and scope of the present invention. Further, regarding the nursery power supply 67, in the preferred embodiment, the nursery unit 24 operates solely on AC power. This is because the nursery unit 24 performs all of the data processing and, thus, requires relatively more power than the sensor unit 22 or the parent unit 26. The nursery unit 24's handling of the data processing, in combination with the low power requirements of the ZigBee® wireless protocol, also allows the sensor unit 22 and parent unit 26 to be able to operate for longer periods of time on a single battery charge. It will be further appreciated that it is advantageous to nevertheless also have a back-up battery as part of the nursery power supply 67 in the event of a power outage.

As best shown in FIGS. 2 and 6, the nursery unit 24 preferably provides a nursery microphone 112. With the nursery unit 24 positioned proximal the child 20's location, the nursery microphone 112 is able to pick up audible sounds made by the child 20. These sounds are then processed by the nursery processor 64 and transmitted to the parent unit 26 via the nursery transceiver 62. The parent speaker 76 then outputs the amplified sounds so that the supervisor is able to monitor the child 20 audibly as well as physically. As shown in FIG. 8, the parent unit 26 provides volume control buttons 114 which allow the supervisor to selectively adjust the volume of the parent speaker 76.

In a further embodiment, as best shown in FIGS. 3 and 7, the parent unit 26 also provides a parent microphone 116. Similar to the nursery microphone 112, with the parent unit 26 positioned proximal the supervisor, and a talk button 118 located on the parent unit housing 68 is pressed, the parent microphone 116 is able to pick up audible sounds made by the supervisor. These sounds are then processed by the parent processor 72 and transmitted to the nursery unit 24 via the parent transceiver 70. The nursery speaker 66 then outputs the amplified sounds so that the child 20 is able to hear the supervisor's voice when desired. Thus, the nursery microphone 112 and parent microphone 116 enable two-way audible communication between the child 20 and the supervisor.

In the preferred embodiment, the present invention is also capable of recording and reproducing a heart beat sound of the supervisor. Studies have shown that ambient noises simulating the sounds heard by a child while in the womb, such as a heart beat, can help the child sleep faster, sleep better, and feel safe. It has been found that ambient noises are most effective when they reproduce the sound of the mother's own heart beat, which the present invention is capable of doing (assuming that the supervisor is in fact the mother). It should be noted that even if the supervisor is not the mother, the supervisor may still record their own heart beat in order to soothe the child 20. To accomplish this, the supervisor first positions the parent microphone 116 against their chest, then presses and holds a record button 120, located on the parent unit housing 68, for a desired period of time. As the parent microphone 116 records the supervisor's heart beat, the parent processor 72 processes the recording and transmits it to the nursery unit 24, where it is stored in a nursery memory 122. The nursery memory 122 stores the recording until it is overwritten by a new recording. The nursery unit housing 60 provides a play button 124 which, when pressed, causes the nursery speaker 66 to continuously output the heart beat recording until the play button 124 is pressed again or the nursery unit 24 is powered off. It should be noted that this is merely an exemplary embodiment of the present invention's ability to record and reproduce a heart beat sound; thus, other means of accomplishing this feature, now known or later developed, may be substituted.

While aspects of the invention have been described with reference to at least one exemplary embodiment, it is to be clearly understood by those skilled in the art that the invention is not limited thereto. Rather, the scope of the invention is to be interpreted only in conjunction with the appended claims and it is made clear, here, that the inventor(s) believe that the claimed subject matter is the invention.

What is claimed is:

1. A baby monitoring system for remotely monitoring a child's breath rate and body orientation, the system comprising:

a nursery unit, a sensor unit, and a parent unit each configured and interoperably connected for wireless communication;

the nursery unit comprising:

a nursery transceiver in wireless communication with the sensor unit and the parent unit;

a nursery processor connected to the nursery transceiver and configured for processing a sensor signal received from the sensor unit, determining the child's breath rate and body orientation, and generating an appropriate display signal for sending to the parent unit; and a nursery speaker configured for generating audible alerts where an alert situation is detected;

the sensor unit comprising an elongate strap configured for removable engagement around the child's abdomen, the strap providing:

at least two tri-axial accelerometers positioned such that, when the strap is engaged around the child's abdomen, a first one of the accelerometers is positioned substantially adjacent the child's belly button, and a second one of the accelerometers is positioned substantially adjacent the child's side each of the accelerometers independently collecting and outputting data related to both the child's breath rate and body orientation, the child's body orientation being one of at least a face-down position, a face-up position, and a sitting-up position;

a sensor processor connected to the accelerometers and configured for receiving outputs from the accelerometers and generating the sensor signal based on the outputs; and a sensor transceiver connected to the sensor processor and configured for transmitting the sensor signal to the nursery unit; and the parent unit comprising:

a parent transceiver configured for receiving the display signal from the nursery unit; a parent processor connected to the parent transceiver and configured for processing the display signal and generating appropriate display data;

a display connected to the parent processor and configured for displaying the display data; and a parent speaker connected to the parent processor and configured for generating audible alerts where an alert situation is detected;

whereby, with the sensor unit removably engaged on the child, the nursery unit positioned proximal the child's location, and the parent unit in the possession of a supervisor, the supervisor is able to remotely monitor the child's breath rate and body orientation.

2. The baby monitoring system of claim 1, wherein the strap of the sensor unit further provides a sensor power supply interconnected with the accelerometers, sensor processor, and sensor transceiver.

3. The baby monitoring system of claim 2, wherein the sensor power supply is a flexible thin film rechargeable battery.

4. The baby monitoring system of claim 2, wherein the strap is configured with at least one selectively openable pocket for receipt therein of the accelerometers, the sensor processor, the sensor transceiver, and the sensor power supply.

5. The baby monitoring system of claim 1, wherein the parent unit and nursery unit each further provide a microphone connected to the respective parent processor and nursery processor for enabling audible communication between the child and the supervisor.

6. The baby monitoring system of claim 1, wherein the display data includes at least one of the child's breath rate per minute, the child's current body orientation, an alert message, the wireless signal strength between each of the sensor unit, nursery unit and parent unit, the sensor unit's battery life, the parent unit's battery life, the nursery unit's power status, and the sensor unit's power status.

7. The baby monitoring system of claim 1, wherein the parent unit further provides an at least one breath rate light configured for flashing in conjunction with the child's breath rate.

8. The baby monitoring system of claim 1, wherein the nursery unit further provides a plurality of indicator lights for displaying system status information.

9. The baby monitoring system of claim 8, wherein the system status information includes at least one of the wireless signal strength between each of the sensor unit, nursery unit and parent unit, the sensor unit's battery life, the parent unit's battery life, the sensor unit's power status, and the parent unit's power status.

10. The baby monitoring system of claim 1, wherein the nursery unit further provides a means for storing and reproducing a heart beat sound.

11. The baby monitoring system of claim 10, wherein the parent unit further provides a record button located on a parent unit housing of the parent unit and electrically connected to the parent processor, the record button triggering the recording of the heart beat sound through a microphone connected to the parent processor, the recorded heart beat sound then being transmitted to the nursery unit by way of the parent and nursery transceivers in cooperation with the parent and nursery processors.

12. A baby monitoring system for remotely monitoring a child's breath rate and body orientation, the system comprising:
- a sensor unit, a nursery unit, and a parent unit each configured and interoperably connected for wireless communication;
- the sensor unit configured for removable engagement about the child's abdomen and comprising:
- at least two tri-axial accelerometers positioned such that, when the sensor unit is engaged about the child's abdomen, a first one of the accelerometers is positioned substantially adjacent the child's belly button, and a second one of the accelerometers is positioned substantially adjacent the child's side, each of the accelerometers independently collecting and outputting data related to both the child's breath rate and body orientation;
- a sensor processor connected to the accelerometers and configured for receiving a plurality of outputs from the accelerometers and generating a sensor signal based on the outputs; and
- a sensor transceiver connected to the sensor processor and configured for transmitting the sensor signal to the nursery unit;

the nursery unit comprising:
- a nursery transceiver in wireless communication with the sensor unit and the parent unit; and
- a nursery processor connected to the nursery transceiver and configured for processing the sensor signal received from the sensor unit, determining the child's breath rate and body orientation, and generating an appropriate status signal for sending to the parent unit; and the parent unit comprising:
- a parent transceiver configured for receiving the status signal from the nursery unit; a parent processor connected to the parent transceiver and configured for processing the status signal and generating appropriate status data; and
- a means for communicating the status data, said means selected from at least one of a display connected to the parent processor and configured for displaying the status data, and a speaker connected to the parent processor and configured for generating audible alerts where an alert situation is detected;

whereby, with the sensor unit removably engaged on the child, the nursery unit positioned proximal the child's location, and the parent unit in the possession of a supervisor, the supervisor is able to remotely monitor the child's breath rate and body orientation.

* * * * *